(12) United States Patent
Lewis et al.

(10) Patent No.: US 6,396,966 B1
(45) Date of Patent: May 28, 2002

(54) GLASS STRUCTURES FOR NANODELIVERY AND NANOSENSING

(75) Inventors: Aaron Lewis; Galina Fish, both of Jerusalem; Sophia Kokotov, Maale Adumim; Edward Khachairyan, Jerusalem; Andrey Ignatov, Jerusalem; Rimma Glazer, Jerusalem; Anatoly Komissar, Jerusalem; Yuri Heifez, Jerusalem; Alina Strinkovsky, Beit Shemesh; Klony Lieberman, Jerusalem, all of (IL)

(73) Assignee: Nanoptics, Inc., Jerusalem (IT)

( * ) Notice: Subject to any disclaimer, the term of this patent is extended or adjusted under 35 U.S.C. 154(b) by 0 days.

(21) Appl. No.: 09/355,336

(22) PCT Filed: Feb. 9, 1998

(86) PCT No.: PCT/US98/01577

§ 371 (c)(1),
(2), (4) Date: Aug. 5, 1999

(87) PCT Pub. No.: WO98/37440

PCT Pub. Date: Aug. 27, 1998

(30) Foreign Application Priority Data

Feb. 9, 1997 (IL) .............................................. 120101

(51) Int. Cl.$^7$ .............................................. G02B 6/00
(52) U.S. Cl. .................. 385/12; 427/163.2; 385/43; 385/146; 385/147
(58) Field of Search ................... 427/163.2; 385/43, 385/12, 38, 147, 146; 65/529; 118/232, 244, 416

(56) References Cited

U.S. PATENT DOCUMENTS

| | | | |
|---|---|---|---|
| 4,233,052 A | * 11/1980 | Dominick et al. | 65/114 |
| 4,310,339 A | * 1/1982 | Blankenship | 118/730 |
| 4,714,488 A | * 12/1987 | Powers | 65/114 |
| 4,743,548 A | 5/1988 | Crossway et al. | |
| 4,877,300 A | 10/1989 | Newhouse et al. | |
| 4,915,467 A | 4/1990 | Berkey | |
| 5,015,843 A | 5/1991 | Seitz et al. | |
| 5,044,716 A | 9/1991 | Berkey | |
| 5,100,507 A | * 3/1992 | Cholewa et al. | |
| 5,137,352 A | 8/1992 | Blitshteyn et al. | |
| 5,361,314 A | * 11/1994 | Kopelman et al. | |

FOREIGN PATENT DOCUMENTS

EP   0545538 A1   6/1993

OTHER PUBLICATIONS

McCulloch, S.; Uttamchandani, D., "A simple reproducible technique for producing sub–micrometre–fibre–optic probes for near–field optical microscopy and chemica sensors," Measurement Science & Technology, IOP Publishing Ltd (Glasgow, UK), vol. 6 (No. 8.), p. 1157–1162, (Aug. 6, 1995).

Smith, N.V.; Royer, W.A.; Rowe, J.E., "Channeling of vacuum ultraviolet radiation down tapered capillaries and prospects for a photoemission spectromicroscopy," Review of Scientific Instruments, American Institute of Physics (Woodbury, NY), vol. 65 (No. 6), p. 1954–1958, (Jun. 13, 1994).

(List continued on next page.)

Primary Examiner—Hung N. Ngo
(74) Attorney, Agent, or Firm—Jones, Tullar & Cooper, P.C.

(57) ABSTRACT

A device comprising a tapered glass structure produced from glass capillary tube by pulling technologies to generate an optimized geometry for high transmission efficiency of electromagnetic radiation. The device being bent near the tip to produce a cantilevered structure suitable for normal force sensing in a variety of attractive, repulsive and non-contact imaging modes.

45 Claims, 5 Drawing Sheets

OTHER PUBLICATIONS

Valaskovic, G.A.; Holton, M.; Morrison, G.H., "Parameter control, characterization, and optimization in the fabrication of optical fiber near–field probes," Applied Optics, Optical Society of American (Washington, DC), vol. 34 (No. 7), p. 1215–1228, (Mar. 1, 1995).

Zeisel, D; Nettesheim, S.; Dutoit, B.; Zenobi, R., "Pulsed laser–induced desorption and optical imaging on a nanometer scale with scanning near–field microscopy using chemically etched fiber tips," Applied Physics Letters, American Institute of Physics, vol. 68 (No. 8), p. 2491–2492, (Apr. 29, 1996).

Betzig, E.; Finn, P.L.; Weiner, J.S., "Combined shear force and near–field scanning optical microscopy," Applied Physics Letters, American Institute of Physics, vol. 60 (No. 20), p. 2484–2486, (May 18, 1992).

Lewis, A.; Lieberman, K., "Probe Microscopy," International Application WO 95/05000, World Intellectual Property Organization, (Feb. 16, 1995).

* cited by examiner

All dimensions are in micrometers

All dimensions are in micrometers

GLASS STRUCTURES FOR NANODELIVERY AND NANOSENSING

1. FIELD OF THE INVENTION

This invention allows the production of tapered straight and cantilevered structures that are optimized for the maximal nanodelivery of electromagnetic radiation and chemicals and for the maximal sensitivity in the nanosensing of ionic phenomena with high efficiency. These structures are generated so that they can simultaneously act as force sensors with excellent dynamic characteristics. Unlike previous attempts at obtaining such elements with chemical etching techniques our methodology is based solely on the application of glass pulling technologies with specific protocols that can minimize the subwavelength travel of light waves and can maximize the dynamic capabilities of these devices. Unlike the glass etching techniques these glass pulling technologies are universally, applicable to glass micropipettes and fibers. In addition optimal geometries of force sensing glass micropipettes are invented for the optimal delivery of chemicals in nanoguantities in a defined and in a nanometrically controlled fashion.

2. BACKGROUND OF THE INVENTION

This invention is based on advances in near-field optics.

Near-field optics is the development of optical elements that can work in the near-field of an object that is to be interrogated by light. In essence, the objective is to develop optical elements that can illuminate, detect and/or enhance optical phenomena within a distance, from the object, that is considerably less than the dimensions of one wavelength. Conventional optical instruments all of which work in the far-field are based on lenses which critically depend on the wave nature of light. Thus, these elements are inherently limited to operation in the far-field with associated problems of diffraction that intrinsically limits resolution to approximately half the wavelength of light. Near-field optical elements not only overcome this diffraction limit of resolution but also relax the wavelength dependence of optical resolution. In its simplest implementation [A. Lewis, M. Isaacson, A. Hartoonian and A. Murray, Biophysical J. 41, 405a (1983); Ultramicroscopy 13, 227 (1984).] near-field optics involves transmitting light through a subwavelength aperture that is brought in close proximity to a surface. The sample or the aperture is then scanned in order to obtain an image or create a pattern with the subwavelength spot of light that emanates from this near-field optical element.

3. STATE OF PRIOR ART

The method of choice that is used throughout the world today to produce near-field optical elements was developed by Lewis et al. [U.S. Pat. No. 4,917,462]. The essence of the methodology of Lewis et al was to use heating, tension and pulling with microprocessor control to produce tapered glass structures that were subsequently coated with metal to form a subwavelength aperture. This was a simple, cheap and reliable method of producing these subwavelength optical elements. Nonetheless, these elements were produced without much regard to the geometry of the subwavelength tip in terms of reducing the subwavelength region through which the light wave traversed. It is important to realize that the technology in the Lewis et al patent was a general methodology for producing these subwavelength tips through which subwavelength points of light could be produced. This generality can be seen by the fact that the same technology could be used to produce tapered optical elements made out of glass capillaries [A. Harootunian, E. Betzig, M. S. Isaacson and A. Lewis, Appl. Phys. Lett. 49, 674 (1986)] or glass fibers [Betzig E., Trautman J. K., Harris T. D., Weiner J. S. and Kostelak R. L., Science 251, 1468 (1991)]. All of these structures, however, had less than optimized geometries at the tip and thus there were significant evanescent losses that resulted from the transmission of the electromagnetic radiation through the tip.

The first attempts at resolving this problem were made by workers who realized that geometries at the tip that were closer to what would be optimal for high transmission of the light wave through the subwavelength region could be approached with chemical etching of glass fibers [Ohtsu, M., S. Juang, T. Pangaribuan and M. Kozuma, Proceesing of NFO-1, 131–139 (1993); Jiang, S., Ohsawa, H., Yamada, K., Pangaribuan, T., Ohtsu, M., Imai, K., and Ikai, A., Jpn. J. Appl. Phys. 31, 2282 (1992)] without any previous tapering. Such structures had the potential to generate high throughputs if the coating of these structures could be effectively performed. The coating, however, was problematic since the etching technology resulted in damaged surfaces that were difficult to impossible to coat successfully. In addition, the angle required for coating such an etched structure was not compatible with the geometry of such untapered etched fibers. Furthermore, the geometry of such untapered elements (see FIG. 1) perturbed significantly the ability of such elements to track rough surfaces. Finally, the untapered nature of these elements made the glass leading to the subwavelength tip very stiff and this crucially reduced the ability of such tips to monitor surface forces. It was this sensitivity of the tapered tips to surface forces [Shalom S., Lieberman K. Lewis A and Cohen S. R., Rev. Sci. Instrm. 63, 4061 (1992)] that allowed the resolution of one of the principle problems of near-field optics which was the ability to bring such a subwavelength tip close to a surface that was to be interrogated. Also none of the etching methodologies could be applied to tapered micropipette structures whereas the pulling technology is applicable to both tapered micropipettes and optical fibers.

In view of all of these factors it would be best if the standard tapering methodology could be extended to produce a high throughput tip that would also be capable of effectively sensing surface forces.

4. SUMMARY OF THE INVENTION

This invention uses pulling technologies as applied to glass tubes to generate without any chemical etching a profile that is ideal to produce a high transmission subwavelength optical aperture with very good atomic force sensing capabilities. The same pulling technology with small amendations can be used to optimize similar structures that can combine force sensing capabilities with such applications as the nanodelivery of materials to surfaces.

5. BRIEF DESCRIPTION OF THE DRAWINGS

The objects, features and advantages of the present invention will be understood by those of skill in the art from the following detailed description thereof, taken with the accompanying drawings, in which:.

6. DESCRIPTION OF THE INVENTION

Figure 1:
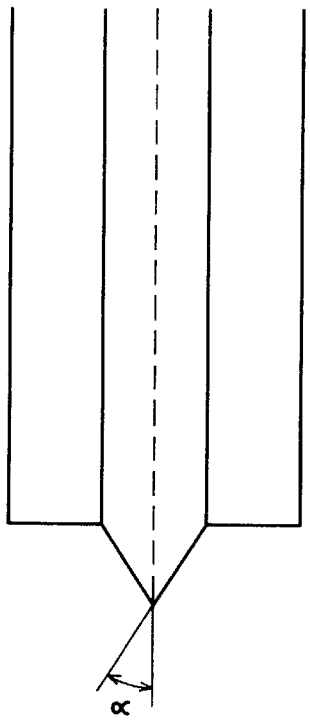
FIG. 1 is a diagrammatic illustration of a glass tube tapered in accordance with the present invention.
Figure 2:
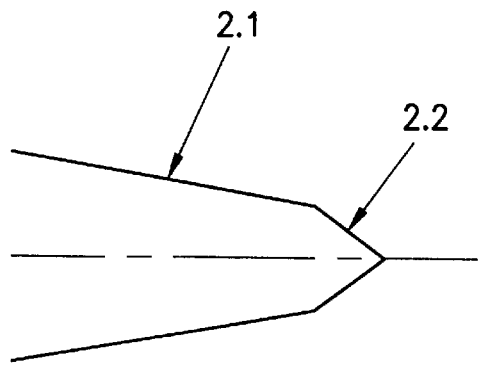
FIG. 2 is a diagrammatic illustration of a tube tapered during a second tapering cycle.

With pulling technology there are many parameters that can be adjusted to obtain the optimal profile. These are: 1. heat or temperature, 2. the geometric region that is heated, called the filament, 3. the velocity of the pulling that is measured as the glass softens and begins to separate under a constant load and this velocity is determined by the time of heating, 4. the delay between the start of the pulling and turning off the heating element and 5. the tension of the pulling. These can all be microprocessor controlled to develop a geometry in which the glass is first tapered to a dimensionality that is above the cut-off for the propagation of electromagnetic radiation in a metallic waveguide (FIG. 2.1 ) and is then cooled before a second tapering cycle is entered in which a cone angle between 30–40° (FIG. 2.2 ) is achieved by multiple pulling cycles. This geometry is shown in FIG. 2. The number of these later cycles depends on the final outer diameter of the tip. In addition to the above these parameters can be altered in order to tailor the devices for other applications such as chemical delivery of materials in nanodimensionalities, optical ion sensing and to optimize the probes for the dynamic movements of the surfaces of the sample initiated by some external stimulus such as light, sound, electricity etc.

5.1 Straight Optical Elements for Maximum Throughpout of Electromagnetic Radiation 5.1.1 Tapered Optical Fibers 5.1.1.1 Pulling The above pulling technology can be applied with the following parameters for straight optical fibers in order to get the maximum powers described in this patent. For the first taper appropriate parameters would be:

| Heat | Filament | Velocity | Delay | Pulling |
|------|----------|----------|-------|---------|
| 250  | 3        | 80       | 250   | 10      |

For the second taper there is a series of three pulls for a 0.1 micron tip with parameters that could be:

| Heat | Filament | Velocity | Delay | Pulling |
|------|----------|----------|-------|---------|
| 250  | 0        | 7        | 150   | 10      |
| 250  | 0        | 10       | 150   | 60      |
| 290  | 0        | 15       | 126   | 100     |

5.1.1.2 Coating

Figure 3:
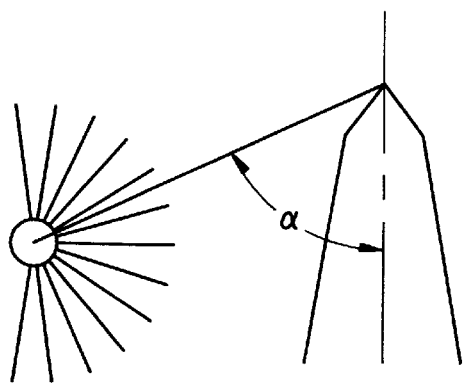
FIG. 3 illustrates a mechanism for coating a tapered optical fiber.

The coating is accomplished with vacuum deposition of metal. One particular example is a thin chrome coating that is then overcoated with a thicker coating of aluminum. For straight elements this coating is accomplished with an angle of 70° between the normal of the optical element and a line drawn between the tip and the filament (see FIG. 3). This angle, $\alpha$, is crucial for the final dimension of the subwavelength aperture at the tip of this second region of taper. The larger the distance between the filament and the tip the more control of the accuracy of the dimension of the aperture. This occurs because the cotan a approaches the cos of this same angle.

5.1.1.3 Force Sensing Capabilities

Figure 4A:
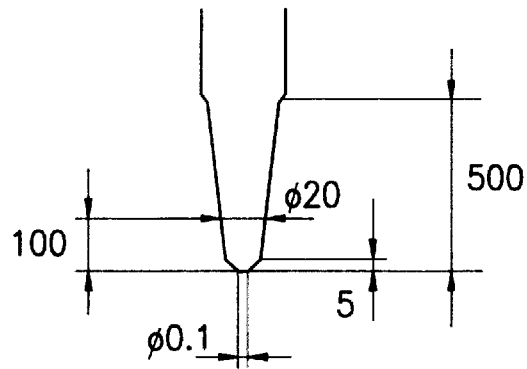
FIG. 4a illustrates a preferred optical fiber taper for force sensing application.

To optimize the force sensing capabilities of these tips the initial taper dimension is chosen to be approximately 20 microns in diameter for region of 100 microns length just above the second taper (see FIG. 4a). This is the region in straight fibers that the flexibility of the structure is monitored. This dimensionality controls the resonance frequency and this frequency, f, can be altered up to 500 kHz with a width of the resonance, $\Delta f$, that can be 0.75 kHz.

5.1.2 Tapered Micropipettes 5.1.2.1 Pulling

Unlike the etching methodologies, the same pulling technology can be also applied to micropipettes. Such micropipettes have important applications in guiding deep ultraviolet light where optical fibers are not effective. To obtain the optimal parameters we use the following protocol:

| Heat | Filament | Velocity | Delay | Pulling |
|------|----------|----------|-------|---------|
| 390  | 15       | 105      | 200   | 20      |

For the second taper there is a series of three pulls for a 0.1 micron tip with parameters that could be:

| Heat | Filament | Velocity | Delay | Pulling |
|------|----------|----------|-------|---------|
| 220  | 0        | 5        | 200   | 18      |
| 200  | 0        | 5        | 200   | 15      |
| 200  | 0        | 30       | 126   | 40      |

5.1.2.2 Coating

The coating is accomplished with vacuum deposition of metal. One particular example is a thin chrome coating that is then overcoated with a thicker coating of aluminum. For straight elements this coating is accomplished with an angle of 700 between the normal of the optical element and a line drawn between the tip and the filament (see FIG. 3). This angle is crucial for the final dimension of the subwavelength aperture at the tip of this second region of taper. The larger the distance between the filament and the tip the more control of the accuracy of the dimension of the aperture. This occurs because the cotan a approaches the cos of this same angle.

5.1.2.3 Force Sensing Capabilities

Figure 4B:
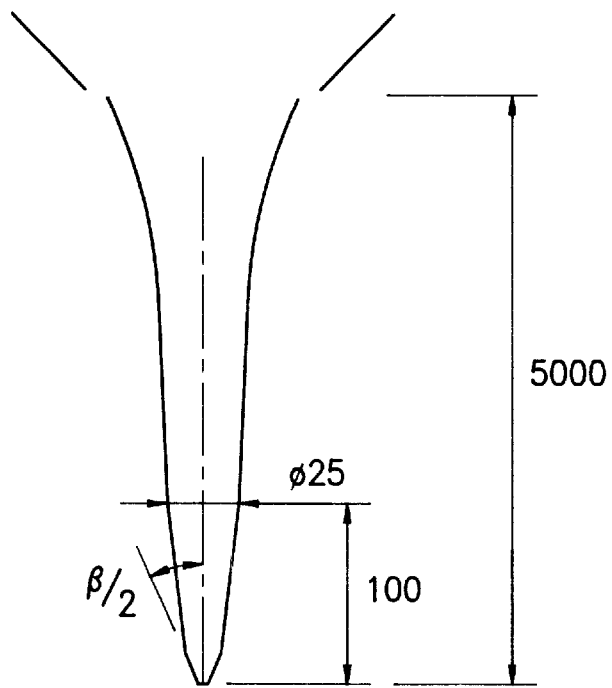
FIG. 4b illustrates a preferred micropipette taper for force sensing applications.

To optimize the force sensing capabilities of these tips the initial taper dimension is chosen to be approximately 25 microns in diameter for region of 100 microns length just above the second taper (see FIG. 4b). This is the region in straight tips that the flexibility of the structure is monitored. This dimensionality controls the resonance frequency and this frequency, f, can be altered up to 60 kHz with a width of the resonance, $\Delta f$, that can be 0.3 kHz.

5.1.3 Cantilevered Fibers

Fibers are bent at the tip according to the procedure that is described by K. Lieberman and A. Lewis, "A Method and a Device for Probe Microscopy" [PCT application Ser. No.

Figure 5:
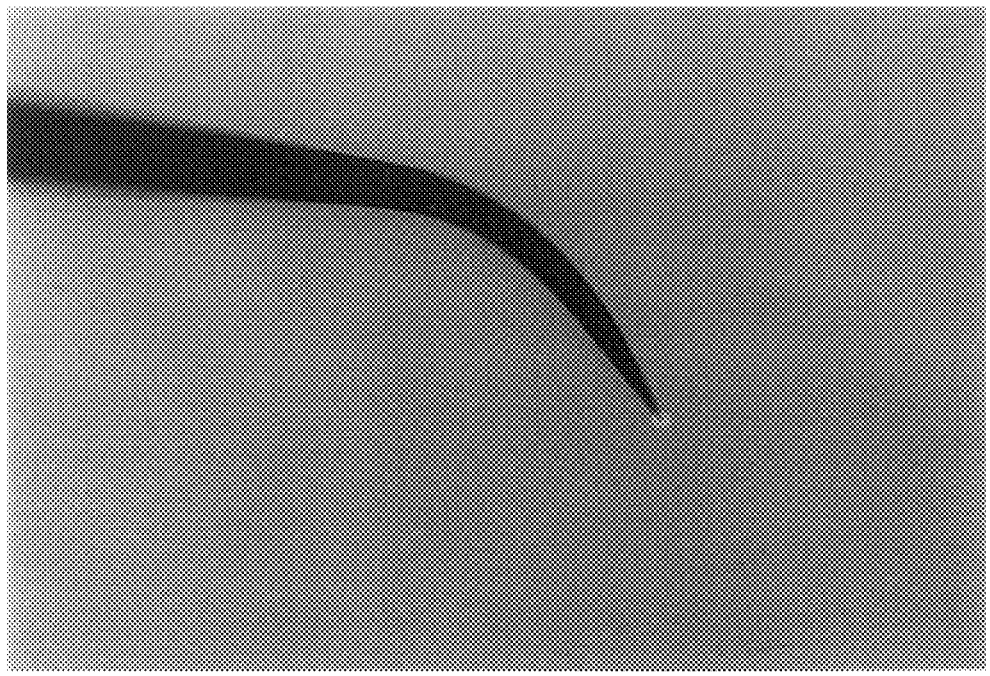
FIG. 5 illustrates a cantilevered bent fiber tip.

PCT/U.S.94/08691]. This bent fiber structure is seen in FIG. 5. The angle of the bend in this structure is between 45–60°. The pulling, coating and the resulting resonance frequencies are the same except that the angle of the coating is 85°. In the case of these cantilevered elements such elements can be used for the dynamic sensing of surface movement initiated by an external stimulus such as light, sound, electricity etc.

5.1.4 Cantilevered Pipettes

The pulling and coating parameters are the same as described above for straight pipettes. However, during the bending operation as described in the Lieberman and Lewis patent application [PCT application Ser. No. PCT/U.S.94/08691] care has to be taken not to block the hollow central core of the pipette. In the case of these cantilevered elements such elements can be used for the dynamic sensing of surface movement initiated by an external stimulus such as light, sound, electricity etc.

5.1.4.1 Cantilevered Pipettes For Light

Figure 6:
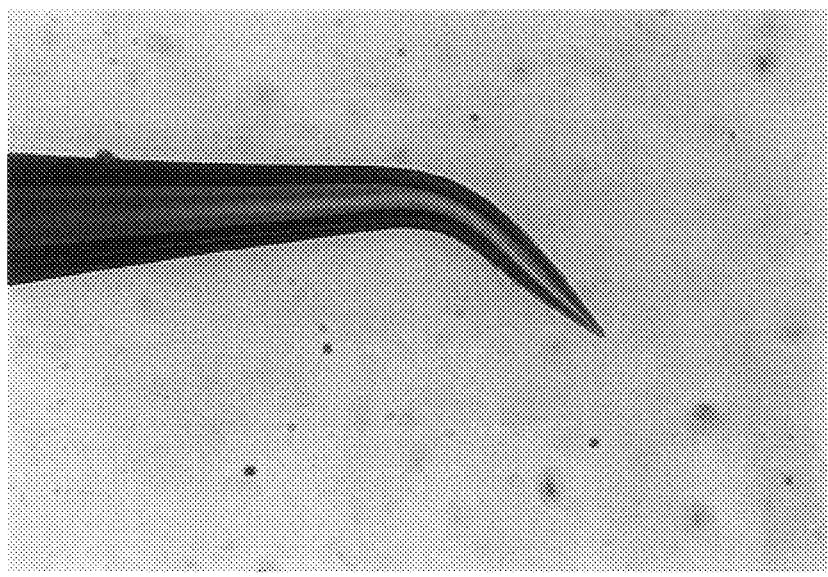
FIG. 6 illustrates a cantilevered pipette constructed in accordance with the invention.

The structure that is obtained by these pulling parameters is shown in FIG. 6. This geometric structure is similar in overall characteristics to what has been obtained with a bent fiber. However, the resonance frequencies that can be achieved for this structure are somewhat lower.

5.1.4.2 Cantilevered Pipettes For Chemistry

In this application a liquid or a gas is transmitted through the narrow opening at the tip of the cantilevered micropipette. Such an uncoated tapered micropipette with force sensing capabilities and a reflective coating only on the cantilever allows the tip to be brought into contact with a surface and this permits the delivery of nanoquantities of material onto the surface. This causes a chemical change on appropriately chosen surfaces if the nature of the chemical in the tip and the chemical in the surface are reactive one with the other.

Figure 7:
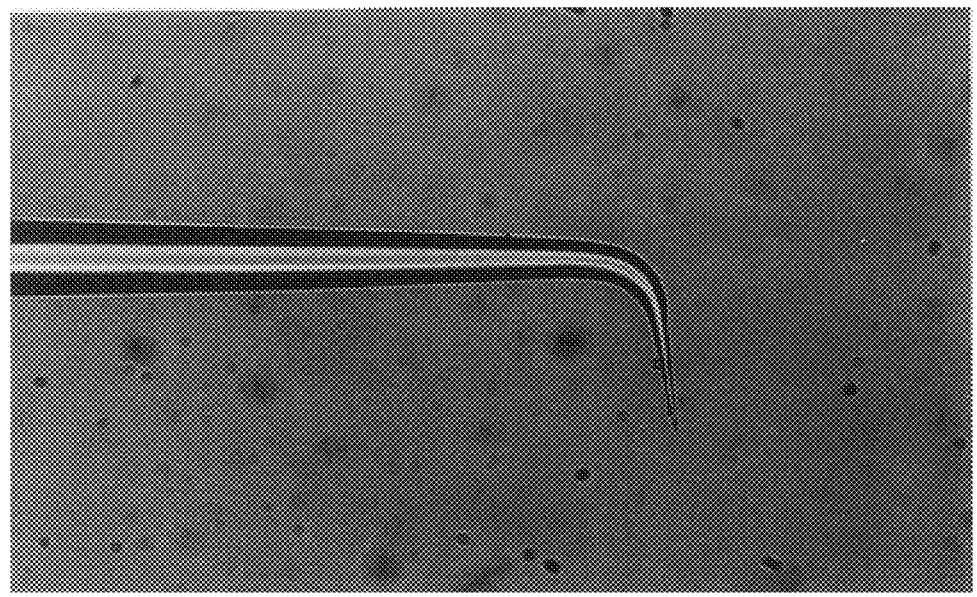
FIG. 7 illustrates a cantilevered pipette used for chemistry.

In the case of a liquid, under one method of control of the liquid that exists, the tip is accomplished by pressure of the liquid column, by chemical manipulation of the hydrophillicity of the surface and the tip and by the nature of the tip geometry. Specifically on this last parameter the requirement is exactly opposite to what is required for the light funnels tips discussed above. When the surface is appropriately wet by the material in the tip the cone angle of the tip can be as small as 7°. This prevents spreading of the liquid column. Measured resonance frequencies of these structures have been measured at 200 kHz. Additional characteristics that are important in such tips is the need to have high resonance frequencies that will allow for intermittent contact operation and to effectively permit imposed resonances on the tip that will allow, in the case of a liquid chemical in the tip, for the column of liquid to be effectively and reproducibly broken. Another characteristic difference for chemicals exiting the tip that wet surfaces is the angle of the bend and this angle can reach 90° instead of the 60° that is more characteristic of the light funnels (FIG. 7). For other surfaces/tip chemical combinations other angles, tip geometries and resonance frequencies have to be chosen for the most appropriate writing with such tips. Also the force sensing capabilities are of importance in order to give the best sensitivity for measuring the chemical alterations on the surface that have occurred.

5.1.4.3 Cantilevered Tapered Micropipettes For Ion Conductance Microscopy

The pulling and coating parameters are similar to those that are described in the tips that are used for chemical delivery.

5.1.4.4 Cantilevered Tapered Micropipettes For Combined Ion Conductance and Optical Ion Sensing The pulling and coating parameters are similar to those that are described in the tips that are used for nanodelivery of light since fibers are inserted to illuminate an ion sensing dye filled sol-gel tip from the inside of the micropipette. An additional characteristic is that the tip has to generate sufficient capillary forces to draw a sol-gel into the tip in which there is a dye which changes in optical characteristics with surrounding ion concentration. These sol-gels are conductive to liquid and can be used for both ion conductance and optical ion sensing. It is best that such structures that are to be used in optics are completely coated with metal as is the case in the optical funnels. Materials other than sol-gels can also be used to act as vessels for these dyes.

5.3 NanoSensing of Surface Dynamics

Optimization of the force sensing capabilities of the probes described above is achieved by modulating the dimension of the taper of the glass in the region where the flexibility of the structure is monitored and this results in a resonance that is controlled in frequency. By controlling this dimension the frequency, f, can be altered by up to 500 kHz with a width of the resonance, $\Delta f$, that can be 0.75 kHz. This allows for maximal response of the tips to dynamic movements of the surface and/or the maximal sensitivity of the tips for the application of non-contact protocols in measuring surface forces.

5.4 A Device for Appropriate Coatinc of the Structures Described Above

Figure 8:
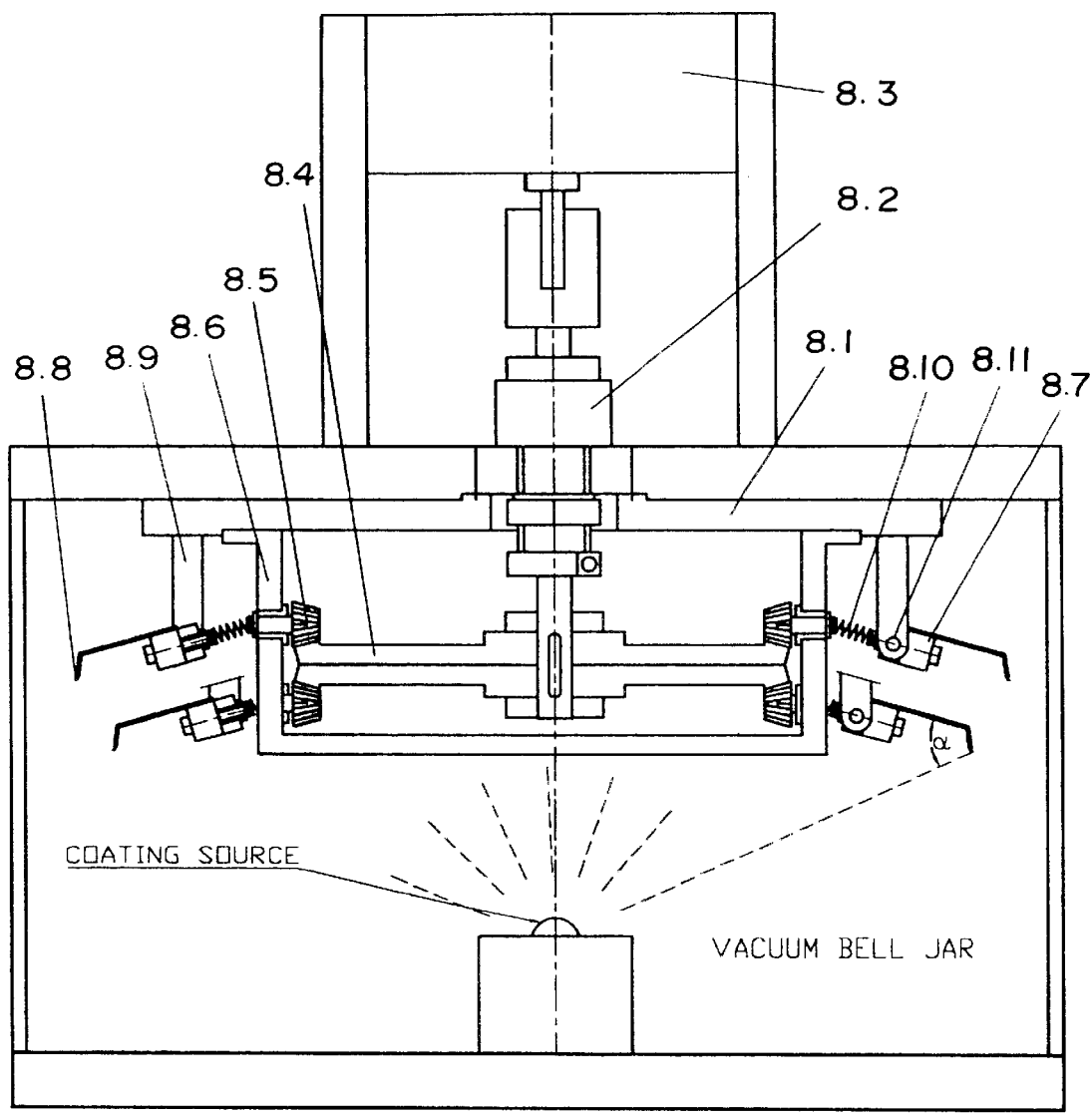
FIG. 8 illustrates a device for applying coating to structures.

To achieve appropriate coatings a device was constructed as shown in FIG. 8. This device is based on vacuum bell jar and consists of a base 8.1, rotating sealed shaft 8.2, electromotor 8.3, drive gear wheel 8.4 and set of driven gear wheels 8.5 that are mounted on the periphery of a cup 8.6. Rotating mounts 8.7 of tapered straight and/or cantilevered micropipettes and fibers 8.8 are mounted on pillars 8.9 and connected with driven wheel axles by flexible shafts 8.10. The device operates as following: The motor 8.3 rotates shaft 8.2, which rotates wheel 8.4 and wheels 8.5. Furthermore, the rotary motion is transmitted on mounts 8.7 with fibers 8.8 by shafts 8.10. The angle of the tapered glass elements may be changed by a mount that can be raised and lowered and can turn around on the axle 8.11. So that the rotation of the tapered straight or cantilevered micropipette or fiber during the coating process provides uniformity of deposition, and its rotation provides the opportunity to prevent the coating of the tip itself.

6. ADVANTAGES OVER PRIOR ART

The techniques described in this patent that can produce high efficiency throughput of light through tapered glass structures with subwavelength apertures at the tip are unique. Previously, all such attempts at producing such structures were based on etching with chemicals. We have achieved high throughputs by inventing a series of pulling protocols that permit very high efficiency transmission of light with excellent capabilities for all force sensing protocols. This has never been achieved before. The throughputs that we have achieved permit the generation of ultrasmall spots of light that could extend to below 20 nm with significant intensities of light in these tips. In addition with small amendations these structures can be altered for excellent delivery of nanoquantities of chemicals with nanometric control of chemistry using the force sensing capabilities of these structures and other uses such as combined force and ion sensing etc.

7. APPLICATIONS

A variety of applications are envisioned in optics, electronics, chemistry, physics and biology where light of small dimensions is required. Where simultaneous force imaging is required correlated with optical images these elements can also be used. In addition the structures that have been amended slightly to deliver nanoquantities of chemicals effectively can also be used in a variety of applications where nanometric control of chemistry is required.

While the invention has been described in its presently preferred embodiment, it will be understood that certain modifications can be made in the basic design without departing from the spirit of the invention as set forth in the appended claims that is appropriately coated with metal that includes a tapered region which is above the cut-off for the transmission of this radiation having a cone angle of 6–10° and a subsequent tapered section that has a much larger cone angle that can be as much as 45° such a structure being optimized for both high throughput light transmission and excellent capabilities for force sensing as a result of having an ultrahigh resonance frequencies for example 500 kHz and a Q factor of 600 and can thus be used in a variety of force sensing protocols. section that has a much larger cone angle that can be as much as 45° such a structure being optimized for both high throughput light transmission and excellent capabilities for force sensing as a result of having an ultrahigh resonance frequencies for example 500 kHz and a Q factor of 600 and can thus be used in a variety of force sensing protocols.

What is claimed is:

1. A device comprised of a tapered glass structure produced from a glass capillary tube by pulling technologies to generate an optimized geometry for high transmission efficiency of electromagnetic radiation, the device being bent near the tip to produce a cantilevered structure suitable for normal force sensing in a variety of attractive, repulsive and non-contact imaging modes.

2. A device as in claim 1 that is cantilevered and optimized for delivery of nanoquantities of liquid in a controlled fashion so that chemistry with nanometric control can be performed and this is accomplished by pressure on the liquid column inside the tapered micropipette, by chemical manipulation of the hydrophillicity of the surface and the tip, by the nature of the tapered geometry of the tip and the angle of the cantilever relative to the tip in order to prevent the spreading of the liquid column on the surface on which nanochemistry is to be performed.

3. A device as in claim 2 with resonance frequencies that will allow for intermittent contact operation and will effectively permit imposed resonances on the tip that will allow, in the case of a liquid chemical in the tip, for the column of liquid to be effectively and reproducibly broken.

4. A device as in claim 2 that is also optimized for maximum force sensitivity.

5. A device as in claim 3 that is also optimized for maximum force sensitivity.

6. A device as in claim 1 that is cantilevered and optimized for ion conductance.

7. A device as in claim 6 that optimizes the transmission of light that can excite either directly or through an optical fiber threaded through the micropipette an ion sensing dye in a sol-gel glass at the tip of the micropipette that is also simultaneously conductive to ions and is also capable of static and dynamic force sensing.

8. A device in which the force sensing capabilities of the probes as described in claim 1 are optimized so that the dimension of the taper of the glass is appropriately chosen in the region where the flexibility of the structure is monitored and this results in a resonance that is controlled in frequency and this frequency, f, can be altered by controlling this dimension up to 500 kHz with a width of the resonance, $\Delta f$, that can be 0.75 kHz and this allows both for maximal response of the tips to dynamic movements of the surface and/or application of non-contact protocols in measuring surface forces.

9. A device in which the force sensing capabilities of the probes as described in claim 1 are optimized so that the dimension of the taper of the glass is appropriately chosen in the region where the flexibility of the structure is monitored and this results in a resonance that is controlled in frequency and this frequency, f, can be altered by controlling this dimension up to 500 kHz with a width of the resonance, $\Delta f$, that can be 0.75 kHz and this allows both for maximal response of the tips to dynamic movements of the surface and/or application of non-contact protocols in measuring surface forces.

10. A device in which the force sensing capabilities of the probes as described in claim 3 are optimized so that the dimension of the taper of the glass is appropriately chosen in the region where the flexibility of the structure is monitored and this results in a resonance that is controlled in frequency and this frequency, f, can be altered by controlling this dimension up to 500 kHz with a width of the resonance, $\Delta f$, that can be 0.75 kHz and this allows both for maximal response of the tips to dynamic movements of the surface and/or application of non-contact protocols in measuring surface forces.

11. A device in which the force sensing capabilities of the probes as described in claim 4 are optimized so that the dimension of the taper of the glass is appropriately chosen in the region where the flexibility of the structure is monitored and this results in a resonance that is controlled in frequency and this frequency, f, can be altered by controlling this dimension up to 500 kHz with a width of the resonance, $\Delta f$, that can be 0.75 kHz and this allows both for maximal response of the tips to dynamic movements of the surface and/or application of non-contact protocols in measuring surface forces.

12. A device in which the force sensing capabilities of the probes as described in claim 5 are optimized so that the dimension of the taper of the glass is appropriately chosen in the region where the flexibility of the structure is monitored and this results in a resonance that is controlled in frequency and this frequency, f, can be altered by controlling this dimension up to 500 kHz with a width of the resonance, $\Delta f$, that can be 0.75 kHz and this allows both for maximal response of the tips to dynamic movements of the surface and/or application of non-contact protocols in measuring surface forces.

13. A device in which the force sensing capabilities of the probes as described in claim 6 are optimized so that the dimension of the taper of the glass is appropriately chosen in the region where the flexibility of the structure is monitored and this results in a resonance that is controlled in frequency and this frequency, f, can be altered by controlling this dimension up to 500 kHz with a width of the resonance, $\Delta f$, that can be 0.75 kHz and this allows both for maximal response of the tips to dynamic movements of the surface and/or application of non-contact protocols in measuring surface forces.

14. A device in which the force sensing capabilities of the probes as described in claim 7 are optimized so that the dimension of the taper of the glass is appropriately chosen in the region where the flexibility of the structure is monitored and this results in a resonance that is controlled in frequency and this frequency, f, can be altered by controlling this dimension up to 500 kHz with a width of the resonance, Δf, that can be 0.75 kHz and this allows both for maximal response of the tips to dynamic movements of the surface and/or application of non-contact protocols in measuring surface forces.

15. A device comprised of a tapered structure produced from an optical fiber by pulling technologies to generate an optimized geometry for high transmission efficiency of electromagnetic radiation, the device being bent near the tip to produce a cantilevered structure suitable for normal force sensing in a variety of attractive, repulsive and non-contact imaging modes.

16. A device in which the force sensing capabilities of the probes as described in claim 15 are optimized so that the dimension of the taper of the fiber is appropriately chosen in the region where the flexibility of the structure is monitored and this results in a resonance that is controlled in frequency and this frequency, f, can be altered by controlling this dimension up to 500 kHz with a width of the resonance, Δf, that can be 0.75 kHz and this allows both for maximal response of the tips to dynamic movements of the surface and/or application of non-contact protocols in measuring surface forces.

17. A method of tapering a glass structure produced from glass tubes by glass pulling technologies to generate an optimized geometry for high transmission efficiency of electromagnetic radiation that is appropriately coated with metal that includes a tapered region which is above the cut-off for the transmission of this radiation having a cone angle of 6–10° and a subsequent tapered section that has a much larger cone angle that can be as much as 45° such a structure being optimized for both high throughput light transmission and excellent capabilities for force sensing as a result of having an ultrahigh resonance frequencies for example 500 kHz and a Q factor of 600 and can thus be used in a variety of force sensing protocols.

18. A method as in claim 17 using a glass capillary.

19. A method as in claim 17 using an optical fiber.

20. A method as in claim 18 that produces a cantilevered structure by bending the tip so that the structure is suitable for normal force sensing in a variety of attractive, repulsive and non-contact imaging modes.

21. A method as in claim 19 that produces a cantilevered structure by bending the tip so that the structure is suitable for normal force sensing in a variety of attractive, repulsive and non-contact imaging modes.

22. A method as in claim 18 that produces a cantilevered structure optimized for delivery of nanoquantities of liquid in a controlled fashion so that chemistry with nanometric control can be performed and this is accomplished by pressure on the liquid column inside the tapered micropipette, by chemical manipulation of the hydrophillicity of the surface and the tip, by the nature of the tapered geometry of the tip and the angle of the cantilever relative to the tip in order to prevent the spreading of the liquid column on the surface on which nanochemistry is to be performed.

23. A method as in claim 22 for producing a structure that has resonance frequencies that will allow for intermittent contact operation and will effectively permit imposed resonances on the tip that will allow, in the case of a liquid chemical in the tip, for the column of liquid to be effectively and reproducibly broken.

24. A method as in claim 22 that also optimizes the structure for maximum force sensitivity.

25. A method as in claim 23 that also optimizes the structure for maximum force sensitivity.

26. A method as in claim 18 for producing a cantilevered structure optimized for ion conductance.

27. A method as in claim 26 for producing a structure that optimizes the transmission of light that can excite either directly or through an optical fiber threaded through the micropipette an ion sensing dye at the tip of the micropipette in a sol-gel glass that is also simultaneously conductive to ions and is also capable of static and dynamic force sensing.

28. A method for the optimization of the force sensing capabilities of the probes as described in claim 26 so that the dimension of the taper of the glass is appropriately chosen in the region where the flexibility of the structure is monitored and this results in a resonance that is controlled in frequency and this frequency, f, can be altered by controlling this dimension up to 500 kHz with a width of the resonance, Δf, that can be 0.75 kHz and this allows both for maximal response of the tips to dynamic movements of the surface and/or application of non-contact protocols in measuring surface forces.

29. A method for the optimization of the force sensing capabilities of the probes as described in claim 27 so that the dimension of the taper of the glass is appropriately chosen in the region where the flexibility of the structure is monitored and this results in a resonance that is controlled in frequency and this frequency, f, can be altered by controlling this dimension up to 500 kHz with a width of the resonance, Δf, that can be 0.75 kHz and this allows both for maximal response of the tips to dynamic movements of the surface and/or application of non-contact protocols in measuring surface forces.

30. A method for the optimization of the force sensing capabilities of the probes as described in claim 19 so that the dimension of the taper of the glass is appropriately chosen in the region where the flexibility of the structure is monitored and this results in a resonance that is controlled in frequency and this frequency, f, can be altered by controlling this dimension up to 500 kHz with a width of the resonance, Δf, that can be 0.75 kHz and this allows both for maximal response of the tips to dynamic movements of the surface and/or application of non-contact protocols in gang measuring surface forces.

31. A method for optimization of the force sensing capabilities of the probes as described in claim 21 so that the dimension of the taper of the glass is appropriately chosen in the region where the flexibility of the structure is monitored and this results in a resonance that is controlled in frequency and this frequency, f, can be altered by controlling this dimension up to 500 kHz with a width of the resonance, Δf, that can be 0.75 kHz and this allows both for maximal response of the tips to dynamic movements of the surface and/or application of non-contact protocols in measuring surface forces.

32. A method for the optimization of the force sensing capabilities of the probes as described in claim 24 so that the dimension of the taper of the glass is appropriately chosen in the region where the flexibility of the structure is monitored and this results in a resonance that is controlled in frequency and this frequency, f, can be altered by controlling this dimension up to 500 kHz with a width of the resonance, Δf, that can be 0.75 kHz and this allows both for maximal response of the tips to dynamic movements of the surface and/or application of non-contact protocols in measuring surface forces.

33. A method for optimization of the force sensing capabilities of the probes as described in claim 23 so that the dimension of the taper of the glass is appropriately chosen in the region where the flexibility of the structure is monitored and this results in a resonance that is controlled in frequency and this frequency, f, can be altered by controlling this dimension up to 500 kHz with a width of the resonance, Δf, that can be 0.75 kHz and this allows both for maximal response of the tips to dynamic movements of the surface and/or application of non-contact protocols in measuring surface forces.

34. A method for the optimization of the force sensing capabilities of the probes as described in claim 25 so that the dimension of the taper of the glass is appropriately chosen in the region where the flexibility of the structure is monitored and this results in a resonance that is controlled in frequency and this frequency, f, can be altered by controlling this dimension up to 500 kHz with a width of the resonance, Δf, that can be 0.75 kHz and this allows both for maximal response of the tips to dynamic movements of the surface and/or application of non-contact protocols in measuring surface forces.

35. A method for the optimization of the force sensing capabilities of the probes as described in claim 22 so that the dimension of the taper of the glass is appropriately chosen in the region where the flexibility of the structure is monitored and this results in a resonance that is controlled in frequency and this frequency, f, can be altered by controlling this dimension up to 500 kHz with a width of the resonance, Δf, that can be 0.75 kHz and this allows both for maximal response of the tips to dynamic movements of the surface and/or application of non-contact protocols in measuring surface forces.

36. A method for the optimization of the force sensing capabilities of the probes as described in claim 17 so that the dimension of the taper of the glass is appropriately chosen in the region where the flexibility of the structure is monitored and this results in a resonance that is controlled in frequency and this frequency, f, can be altered by controlling this dimension up to 500 kHz with a width of the resonance, Δf, that can be 0.75 kHz and this allows both for maximal response of the tips to dynamic movements of the surface and/or application of non-contact protocols in measuring surface forces.

37. A method as in claim 18, that produces a cantilevered structure for delivering nanoquantities of material in a controlled fashion.

38. A method as in claim 18, that produces a cantilevered structure for delivering nanoquantities of fluid in a controlled fashion.

39. A method for optimization of the force sensing capabilities of the probes as described in claim 20 so that the dimension of the taper of the glass is appropriately chosen in the region where the flexibility of the structure is monitored and this results in a resonance that is controlled in frequency and this frequency, f, can be altered by controlling this dimension up to 500 kHz with a width of the resonance, Δf, that can be 0.75 kHz and this allows both for maximal response of the tips to dynamic movements of the surface and/or application of non-contact protocols in measuring surface forces.

40. A method for the coating of tapered straight and cantilevered glass structures having straight glass tips so that thin films can be deposited on these glass structures by rotation about the axis of the straight glass tip and by accurately varying the angle of incidence between the film source and the tip target.

41. A method for the optimization of the force sensing capabilities of the probes as described in claim 40 so that the dimension of the taper of the glass is appropriately chosen in the region where the flexibility of the structure is monitored and this results in a resonance that is controlled in frequency and this frequency, f, can be altered by controlling this dimension up to 500 kHz with a width of the resonance, Δf, that can be 0.75 kHz and this allows both for maximal response of the tips to dynamic movements of the surface and/or application of non-contact protocols in measuring surface forces.

42. A method for the coating of tapered straight and cantilevered structures for maximal throughput of electromagnetic radiation by controlling the distance accurately between the point of evaporation and the tip of the straight micropipette or fiber or the cantilever of the bent micropipette or fiber and this distance control is related to the diameter of the central rotator of all the tips so that the cotan of the angle between the axis of the straight micropipette or fiber or the cantilever of the bent micropipette or fiber approaches the cos of this same angle.

43. A method for the coating of tapered straight and cantilevered structures for maximal throughput of electromagnetic radiation by controlling the angle of incidence of deposition of a thin film coating together with the distance as in claim 32 to give most accurate control of the final dimension of the resulting aperture at the tip and controlling the thickness of the coating for maximum throughput of electromagnetic radiation.

44. A device for the coating of tapered straight and cantilevered structures having tips for maximal throughput of electromagnetic radiation by accurately controlling the distance between a point of evaporation and the tips of the structures, this distance control being related to the diameter of a central rotator of all the tips so that the cotan of the angle between the axes of the structures approaches the cos of this same angle.

45. A device for the coating of tapered straight and cantilevered structures for maximal throughput of electromagnetic radiation by controlling the angle of incidence of deposition of a thin film coating together with the distance as in claim 10 to give most accurate control of the final dimension of the resulting aperture at the tip and controlling the thickness of the coating for maximum throughput of electromagnetic radiation.

\* \* \* \* \*

UNITED STATES PATENT AND TRADEMARK OFFICE
CERTIFICATE OF CORRECTION

PATENT NO. : 6,396,966 B1 Page 1 of 1
DATED : May 28, 2002
INVENTOR(S) : Aaron Lewis et al.

It is certified that error appears in the above-identified patent and that said Letters Patent is hereby corrected as shown below:

<u>Column 12,</u>
Line 35, replace "32" with -- 42 --.
Line 51, replace "10" with -- 44 --.

Signed and Sealed this

Twentieth Day of August, 2002

*Attest:*

JAMES E. ROGAN
*Attesting Officer*     *Director of the United States Patent and Trademark Office*